United States Patent [19]

Iskander

[11] Patent Number: 4,488,559
[45] Date of Patent: Dec. 18, 1984

[54] APPARATUS AND METHOD FOR MEASURING LUNG WATER CONTENT

[75] Inventor: Madgy F. Iskander, Salt Lake City, Utah

[73] Assignee: University of Utah, Salt Lake City, Utah

[21] Appl. No.: 279,102

[22] Filed: Jun. 30, 1981

[51] Int. Cl.³ .............................................. A61B 5/08
[52] U.S. Cl. .................................... 128/653; 128/716
[58] Field of Search ................ 128/653, 716, 736, 804

[56] References Cited

U.S. PATENT DOCUMENTS

| | | | |
|---|---|---|---|
| 4,162,500 | 7/1979 | Jacobi et al. | 128/653 X |
| 4,240,445 | 12/1980 | Iskander | 128/804 |
| 4,346,716 | 8/1982 | Carr | 128/804 X |

OTHER PUBLICATIONS

Graf, Modern Dictionary of Electronics, "Dielectric", Third Edition, 1970.
Iskander and Durney, *Medical Diagnosis and Imaging Using Electromagnetic Techniques*, Proc. of NATO Advanced Study Institute, on Theoretical Methods for Determining the Interaction of Electromagnetic Waves with Structures, Norwich, England, (Jul. 23-Aug. 4, 1979).
Iskander and Durney, *Electromagnetic Techniques for Medical Diagnosis; A Review*, 68 Proc. of the IEEE 1, (Jan. 1980).
Barrett et al., Science, vol. 190, Nov. 14, 1975, pp. 669-671.
Bragg et al., Investigative Radiology, May-Jun. 1977, pp. 289-291.

*Primary Examiner*—Kyle L. Howell
*Assistant Examiner*—John C. Hanley
*Attorney, Agent, or Firm*—Workman, Nydegger & Jensen

[57] ABSTRACT

A microwave radiometer for the passive, noninvasive measurement of fluid content in animal bodies. The radiometer system includes a ridged waveguide antenna which is responsive to frequencies in the microwave range emitted from the patient's body and is of compact size and light in weight so as to be easily secured to the patient with minimum discomfort and loss of mobility. A heating system is attached to the antenna so as to maintain antenna temperature at approximately the temperature of the patient's body surface. The associated control circuitry processes signals received from the antenna at one or more frequencies and produces an output signal which correlates to the amount of fluid within the measured region of the body.

20 Claims, 6 Drawing Figures

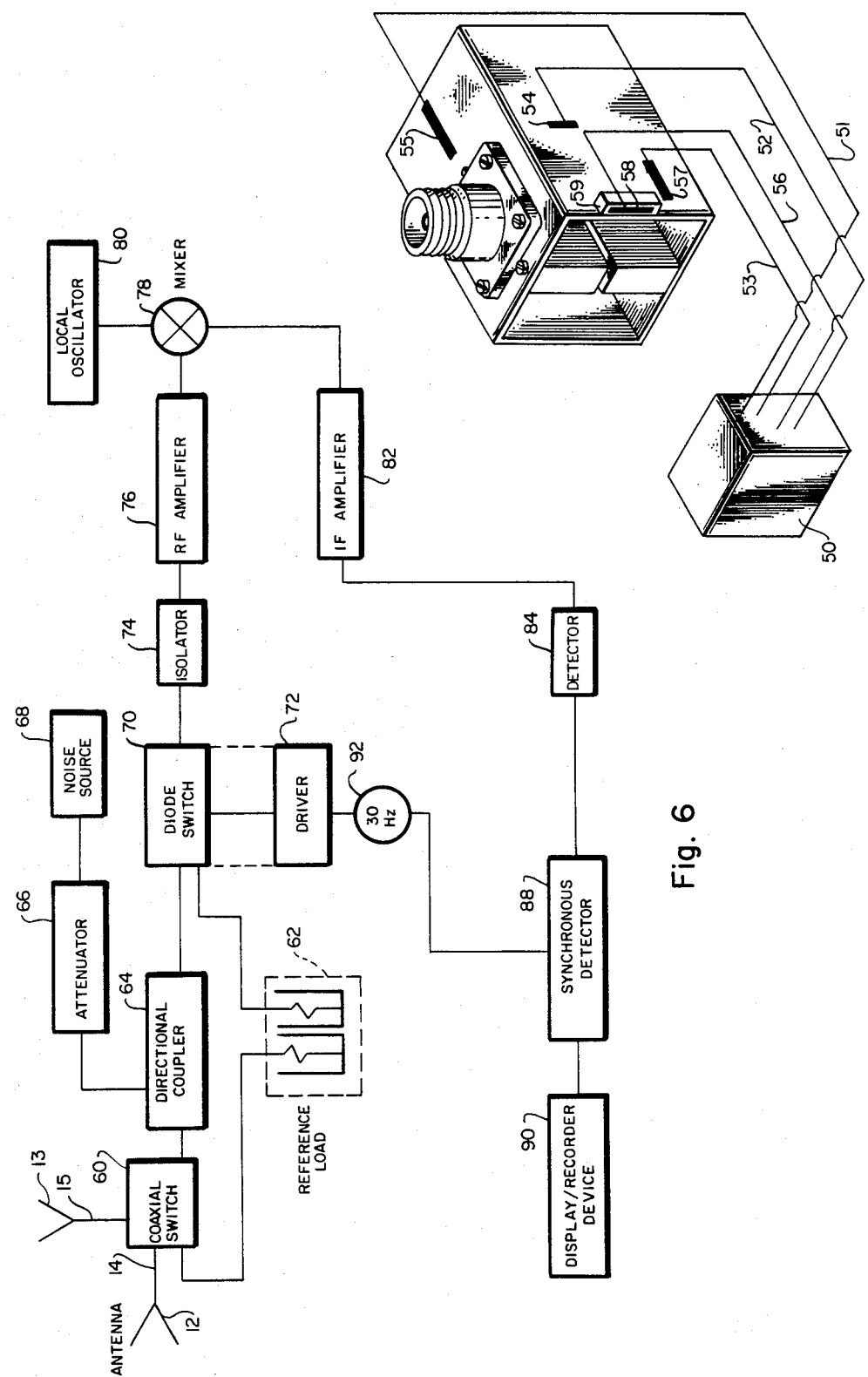

APPARATUS AND METHOD FOR MEASURING LUNG WATER CONTENT

BACKGROUND

1. Field of the Invention

The present invention relates to the measurement of lung water content, and more particularly, to apparatus and methods for passive, noninvasive determination of lung water content and distribution through the measurement of electromagnetic radiation emitted naturally by the animal body.

2. The Prior Art

It is well known in the medical arts that the change in lung water content is an important and useful parameter in medical diagnostics. Changes in the water content of the lung sre symptomatic of numerous medical and surgical abnormalities. For example, in almost all pulmonary abnormalities occuring in patients with heart disease or critical burns, changes in lung water content or distribution are detectable. Thus, the monitoring of such changes in the lung water content can facilitate the early identification of such abnormalities.

Although a means for the accurate measurement of changes in lung water content could be an extremely valuable diagnostic tool, those devices and methods which are currently known and used by medical practitioners have many deficiencies. Presently known methods are incapable of sensitive measurement, overly complicated and elaborate, and time-consuming to use. In addition, these methods require highly skilled technicians for their operation, involve exposing the patient to possibly dangerous radiation, and are not suitable for continuous monitoring which is desirable for most applications and is essential for critically ill patients.

Historically, one widely used method for attempting to identify changes in lung water content has been to monitor the lung with the chest radiograph. However, this method is very insensitive, often requiring a doubling of total lung water content before changes can be detected on the x-ray photographs. As a result, this radiographic method is only reliable as a basis for diagnosis in the most advanced cases. Furthermore, because of the hazardous effects of long term or excessive exposure to x-rays, this method cannot be used for continuously monitoring the patient.

Another technique which as been used for detecting changes in lung water content is electrical impedance ("EI") plethysmography. The basic idea behind this low-frequency electromagnetic method is that when a low frequency voltage is applied across an isolated lung, the measured current is a result of the movement of ions in extracellular water. Theoretically, since air constitutes the major component of the lung's volume, the resistance of the lung should be high so that this method should be sensitive to changes in blood and extracellular volumes. However, disappointing in vivo measurements have been obtained from this method due to the short-circuiting effect of the more conductive surrounding tissues, such as the medistinum and the chest wall. This short circuiting effect significantly reduces the sensitivity of the method, with the result that rather large changes in lung water content are again necessary before any clear detection of a change is possible.

Subsequent improvements of these methods include the addition of guarded electrodes and focusing electrode bridges in conjunction with EI plethysmography. Although these improvements have given the EI plethysmography method an improved sensitivity, the improvement has not been significant and has only resulted in a sensitivity similar to that obtained from the chest radiograph.

Therefore, techniques such as these for measuring the changes in lung water content have not proved acceptable for most diagnostic purposes which require sensitive identification of small changes in the quantity of water contained in the lung.

Several recent attempts to provide more sensitive measurements of changes in lung water content have involved the use of penetrating microwave radiation. Such methods are based upon the fact that variations in lung water content cause a change in the permittivity and the conductivity of the lung tissue, thereby changing the absorption characteristic of the transmitted microwave signals.

One of these methods utilizes electromagnetic waves which are attenuated as they travel through the body. Although this method has been shown to have much greater sensitivity than those methods previously discussed, it has been found to be difficult to use this method with actual patients. This method requires use of both a transmitter and a receiver, each positioned upon opposite sides of a body so that signals can be transmitted therebetween; the lung water content is determined by the measured changes in the magnitude and phase of the transmitted signal.

The problems with this method result from the necessity for accurate alignment of the transmitter and receiver, which alignment should be maintained during the entire course of the series of measurements. Thus, during such monitoring, simple movements by the patient (such as changing position in bed, moving the arms or legs, and stretching) cause alignment problems between the transmitter and receiver such that inaccurate and unreliable measurements result. In addition, since this method involves the transmission of microwaves through a human body, the possible deleterious effects on the patient's health preclude its application in a continuous monitoring technique.

A further problem experienced with prior art methods and systems directed to the use of microwaves for monitoring biological bodies is associated with attempts to reduce the size and weight of the microwave antenna while providing for impedance matching between the antenna and the biological body. One device which is somewhat reduced in size over other types of microwave antennas is the ridged waveguide. This type of waveguide provides a means for lowering the cutoff frequency in order to monitor at lower operating frequencies or, alternatively, for using a smaller aperture size.

To further reduce the required size of the aperture or to permit still lower frequency operation, dielectric loading is employed. Typically, dielectric loading is accomplished by securing dielectric material in the aperture of the waveguide. One adverse result of adding dielectric is that the weight of the antenna increases, thus making it more difficult to secure the antenna in an immobile position on the patient, and making the antenna more uncomfortable for the patient to wear. Furthermore, because of the increased mass resulting from dielectric loading, it becomes more difficult to reach and maintain an antenna temperature level which substantially equals the temperature of the adjacent biological body. It would be an improvement in the art to provide small, lightweight, dielectric free microwave antennas which are adjustable to approximate the impedance of the biological body in an air medium and which are readily adaptable for use in passive, non-invasive monitoring.

In light of problems such as these, which have been encountered in the techniques heretofore known in the art, it would be a substantial improvement to provide a passive, noninvasive system for measuring changes in lung water content which is both sensitive and accurate so as to identify even small changes in lung water content. It would be even more significant if this system were clinically safe for use in long term continuous monitoring of lung water content within the human body.

BRIEF SUMMARY AND OBJECTS OF THE INVENTION

The present invention relates to a technique for detecting changes in lung water content through the use of a low frequency microwave antenna and associated circuitry which is capable of measuring low frequency microwave signals emitted from human or animal bodies. The microwave antenna makes radiometric measurements in the frequency spectrum of the radiation emitted by the body, and in particular from the lung. These measurements are processed in associated circuitry so as to identify and minimize noise and other phenomena, thereby improving the accuracy of measurement. The resulting signal provides information which can be related to relevant medical parameters necessary for the making of a diagnosis of medical and surgical abnormalities.

To provide more accurate data and results, a method for making multiple measurements at different frequencies is also disclosed. The frequency range for such additional measurements may include measurements at microwave frequency levels or at millimeter wavelength levels by utilizing a millimeter wave antenna and waveguide in combination with the same electronic circuitry as is used with the microwave antenna.

It is, therefore, a primary object of the present invention to provide an improved radiometer and method for use in measuring fluid content in living bodies.

It is another object of the present invention to provide a radiometer which is capable of and safe for continuous monitoring a fluid content in specified regions of living bodies.

It is a further valuable object of the present invention to provide a noninvasive, passive method and apparatus for monitoring fluid content within specified regions of living bodies which can be practically used in the typical medical or surgical environment.

It is still a further object of the present invention to provide an apparatus which may be affixed adjacent the surface of a living body so as to permit freedom of movement while providing continuous, highly sensitive monitoring of changes in lung water content.

It is also an object of the present invention to provide a radiometer for measuring fluid content within specified regions of animal bodies which requires only one microwave antenna for accomplishing such measurements.

These and other objects and features of the present invention will become more fully apparent from the following description and appended claims taken in conjunction with the accompanying drawings.

BRIEF DESCRIPTION OF THE DRAWINGS

FIGS. 5 is a front perspective view of a preferred microwave radiometer antenna including a schematic representation of its interconnection with a preferred embodiment of a temperature control system.

FIG. 6 is a block diagram of the circuitry of one preferred embodiment of a microwave radiometer used in conjunction with this invention.

DETAILED DESCRIPTION OF THE PREFERRED EMBODIMENT

The invention is best understood by reference to the drawings wherein like parts as designated with like numerals throughout.

1. General Discussion

The use of radiometry in medical applications is possible due to the fact that all bodies above absolute zero temperature emit energy in the form of electromagnetic radiation. The frequency at which the maximum radiation occurs depends upon the body temperature. For temperatures of practical medical interest, the maximum radiation occurs in the infrared region. The amount of radiation is dependent upon the emissivity; therefore, by measuring changes in the emitted energy, it is possible to detect variations in the dielectric properties, relative dimensions, and temperature within the measured region.

The greatest advantage of measuring emitted radiation at microwave frequencies is the greater penetration depth of this type of radiation over that of infrared radiation. This means that microwave radiation emitted from structures deep within the body may be measured, whereas it may be difficult to measure the infrared radiation emitted from deep within the body. However, since microwave radiometers operate at lower frequencies, thus having longer wavelengths, they provide for courser spacial resolution than infrared thermography. The trade-off between penetration depth and necessary resolution is the major consideration in determining the desired operating frequency range for use of this method.

For applications involving use of the invention disclosed herein, and especially with respect to monitoring changes in lung water content, a reasonable range for frequency monitoring has been found to be between about 500 megahertz ("MHz") and about 12 gigahertz ("GHz"), with the more preferable range being between about 750 MHz and about 1.5 GHz. Solely for purposes of example in this discussion, a frequency of 1 GHz has been chosen as the operating frequency, however, it will be readily appreciated that other operating frequencies could have been chosen.

2. The Apparatus of the Present Invention

Figure 1:
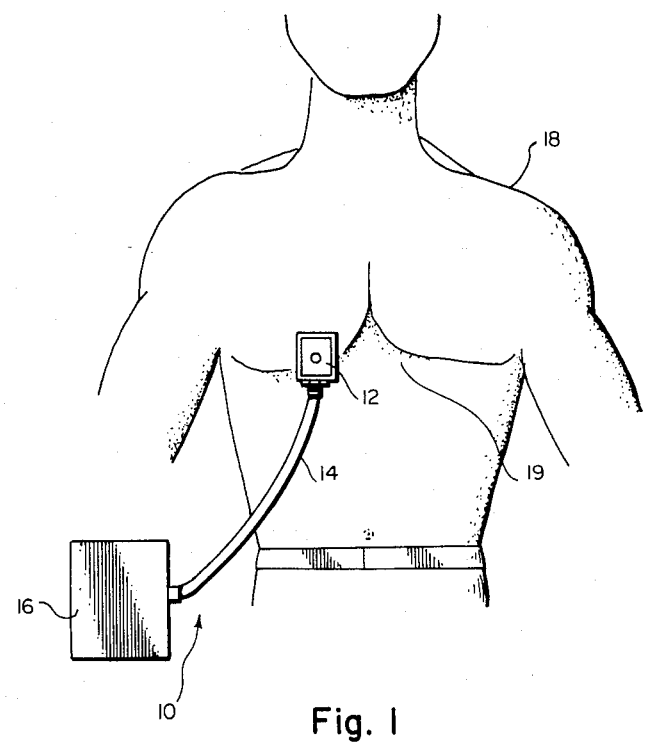
FIG. 1 is a schematic representation of one preferred embodiment of the invention for monitoring water content within living bodies.

Referring to FIG. 1, the radiometer of this invention is shown generally at 10 and includes an antenna 12 coupled by a coaxial cable 14 to a suitable receiver indicated schematically at 16. Antenna 12 is shown placed against the chest 19 of a patient 18 for the purpose of detecting lung water content as will be described more fully hereinafter.

Figure 2:
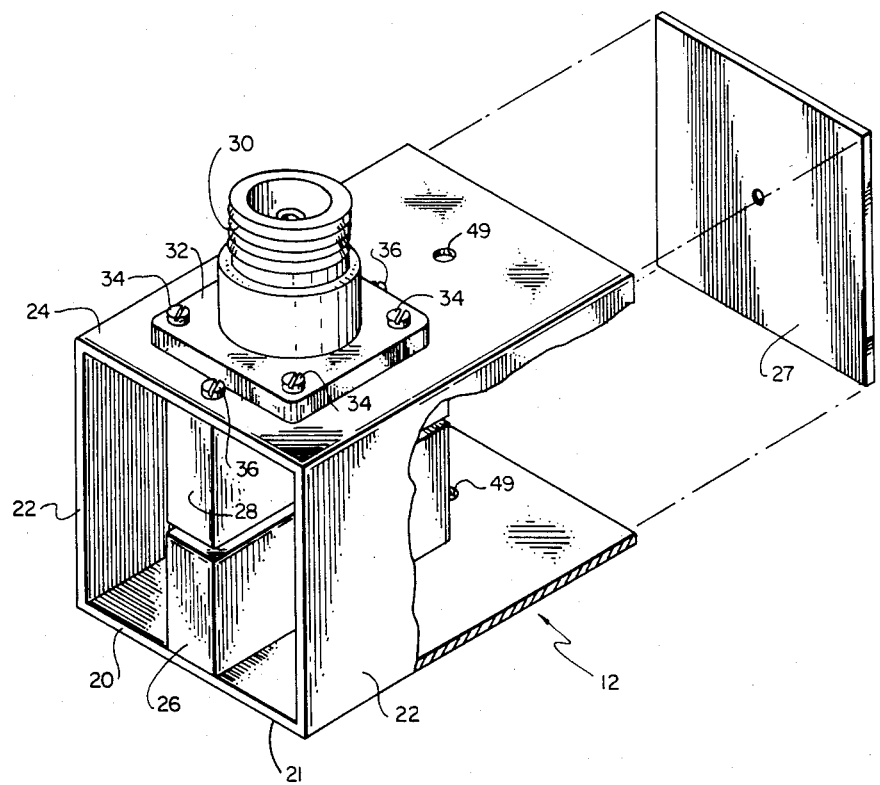
FIG. 2 is a front perspective view of a preferred microwave radiometer antenna showing the back plate separated from the body and having parts cut away so as to reveal the interior structure.

Referring now more particularly to FIG. 2, antenna 12 is comprised of a ridged wave-guide antenna which includes a housing 21 having a base 20, sides 22, top 24, and a removable back plate 27. Housing 21 is typically of metallic construction, preferably comprised of materials such as brass or copper.

Positioned upon the interior surface of base 20 is a bottom wave-guide ridge member 26 comprising a rectangular shaped block of a metallic material such as aluminum. The front end of ridge member 26 is positioned near the forward open end of housing 21 with its body extending into housing 21 parallel to sides 22, with the back end of ridge member 26 being positioned well in front of the back end of housing 21.

Affixed to the interior face of top 24 is a top wave-guide ridge member 28 which is identical to ridge member 26 and is positioned so that its bottom face is in parallel alignment with the top face of ridge member 26. The relative positioning and size of ridge members 26 and 28 directly affects the characteristic impedance of the antenna.

It has been found that the characteristic impedance of the human body is typically about 50 ohms at frequencies near 1 GHz. Therefore, in order to optimize the signal transfer across the interface between the patient's chest 19 and antenna 12, ridge members 26 and 28 are sized and positioned so that the characteristic impedance of antenna 12 is approximately 50 ohms at frequencies near 1 GHz.

Attached to the exterior of top 24 is a coaxial end connector 30. Connector 30 is secured by a plate 32 which is fastened to the surface of top piece 24 by means of screws 34. Connector 30 is positioned upon top 24 so as to be vertically aligned with the center portion of ridge members 26 and 28 so that it may be connected thereto in a manner which will be more fully described hereafter.

Back plate 27 is configured so that its edges conform snugly to the inner surfaces of housing 21 (that is, the interior surfaces of face 20, sides 22, and top 24). Back plate 27 is thus held within the body of antenna 24, but it may be slidably positioned within the housing behind ridge members 26 and 28. Adjustment of the position of back plate 27 causes a change in the characteristic impedance of the antenna 12, thereby modifying the frequency received by the antenna.

Top wave-guide rigde member 28 is secured to the interior surface of top 24 by means of screws 36. Bottom wave-guide ridge member 26 is secured to base 20 in a similar manner by screws 40, as illustrated in FIGS. 3 and 4.

Figure 3:
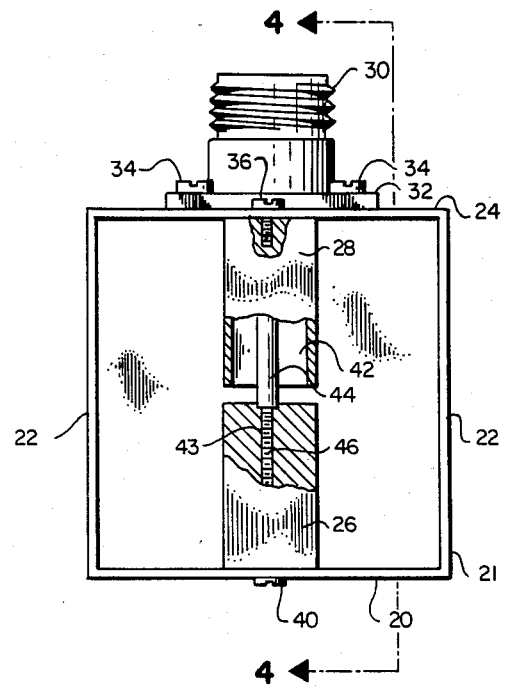
FIG. 3 is a front elevational view of the microwave radiometer antenna of FIG. 2 having parts cut away to reveal the interior construction of the ridges.
Figure 4:
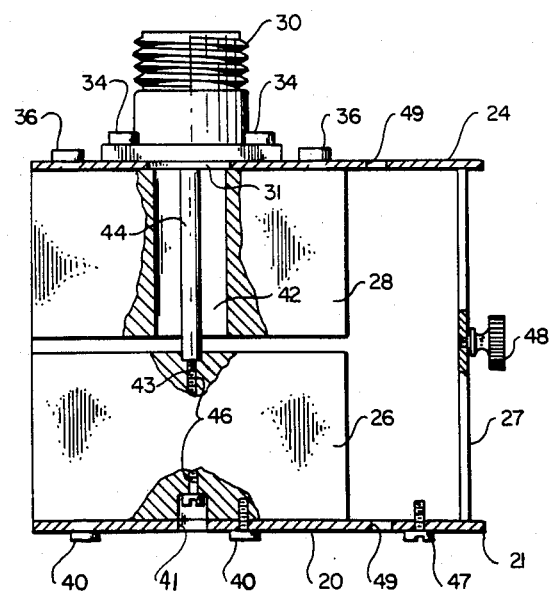
FIG. 4 is a side sectional view of the microwave radiometer antenna taken along lines 4—4 of FIG. 3 and having parts cut away to reveal the internal construction of the ridges.

The means by which coaxial end connector 30 is connected to the ridge members 26 and 28 is shown in FIGS. 3 and 4. Positioned directly beneath connector 30 is an aperture 31 in top 24 (see FIG. 4). A cylindrically shaped bore 42 extends from the top to the bottom of top wave-guide ridge member 28, with this bore 42 being additionally in direct alignment with the aperture in top 24. A second cylindrically shaped bore 43 extends from the bottom to the top of bottom wave-guide ridge member 26; bore 43 has a smaller diameter than bore 42 and is in axial alignment with the center of bore 42.

A center conductor 44 extends downwardly from the center of connector 30 through bore 42 and into bore 43 so as to contact the interior surface of bore 43. As shown in FIG. 4, conductor 44 is secured within bore 43 by means of a securing screw 46 of FIG. 4. Screw 46 is threadably connected to the interior threaded surface of the lower end of conductor 44 and is positioned within bore 43 through an aperture 41 in base 20 which is in alignment with bore 43. The lower portion of through bore 43 is preferably of a greater diameter than the remainder of that bore so that the threaded portion of screw 46 may be inserted within the smaller diameter portion of bore 43, and the head of screw 46 may be recessed within the larger diameter portion of the bore.

As is apparent from FIG. 4, handle 48 is attached to the center of back plate 27 and is used to adjust the position of back plate 27 within housing 21. In order to secure back plate 27 in a desired position, one or more screws 47 may be threadably inserted through apertures 49 which are positioned rearward of ridge members 26 and 28.

In addition to matching the impedance of antenna 12 to that of the body 18, it is also desirable to maintain the temperature of antenna 12 at substantially the same temperature as the patient's chest 19. If there is a difference between the temperature of antenna 12 and the chest surface, a temperature gradient exists. Since the radiometric signal which is measured by this apparatus is temperature sensitive, the presence of this temperature gradient can cause a significant reduction in the accuracy of the measurement.

Accordingly, as is illustrated in FIG. 5, the presently preferred embodiment of the invention avoids the problems caused by such temperature gradients by incorporating a temperature control system 50. In such a system, a commercially available thermostat is connected through an electrical lead 52 to a thermistor 54 which is positioned on antenna 12 so as to detect the temperature of the antenna. Temperature control system 50 is also connected through electrical lead 56 to a second thermistor 58 which is affixed to a support device 59 so as to be positioned adjacent to but not in thermal contact with antenna 12. Thermistor 58 is positioned such that when the front portion of antenna 12 is placed against the patient's chest 19, as depicted in FIG. 1, thermistor 58 will be in contact with the chest surface, thereby sensing the temperature of the chest surface.

Temperature control device 50 is also connected through electrical leads 51 and 53 to heating devices 55 and 57, respectively. Heating devices 55 and 57 may consist of any commercially available direct application heater which is remotely controllable and which may be affixed to the surface to be heated.

In actual operation, the heating arrangement described in FIG. 5 functions such that thermistors 54 and 58 transmit electronic signals which correspond to the temperatures which they measure. Temperature control device 50 compares the temperature of antenna 12 as determined by thermistor 54 with the temperature of the patient's chest 19, as determined by thermistor 58. If temperature control device 50 determines that the temperature of antenna 12 is lower than that of body 18, it will activate heaters 55 and 57 so as to cause the temperature of antenna 12 to increase to that of body 18. When temperature control device 50 determines that the temperature of antenna 12 is approximately equal to that of body 18, it will deactivate heaters 55 and 57 so as to prevent further heating of antenna 12.

Although one preferred embodiment of antenna 12 has been described above, it is clear that numerous other antenna types could also be used so as to produce acceptable results. One such antenna is described in the patent application of myself and Carl H. Durney, which is identified as U.S. patent application Ser. No. 954,054, filed Oct. 23, 1978, now issued as U.S. Pat. No. 4,240,445 to Magdy F. Iskander et al. The description of the antenna of that application is hereby incorporated by reference in order to describe an alternate embodiment of an antenna which may be used in this invention.

One skilled in the art will recognize that there are many other commonly available printed circuit antennas which are small in size and light in weight and which could be used in practicing this invention. The physical size of the antenna, its match to the impedance of the body, and the possibility of its operation over a broad frequency band are all basic design criteria which must be considered in selecting the receiving antenna.

Still another preferred antenna for use with this system comprises a focused antenna which does not require contact with the surface of chest 19. The direct contact antenna 12 described above is desirable because of the significant sensitivity which may be achieved through proper impedance and temperature matching between antenna 12 and chest 19. However, it is sometimes difficult to obtain adequate resolution of the received electromagnetic signals with this type of antenna, particularly when monitoring subcutaneous tissues at depths of 2 centimeters or more below the surface of the body. This is true since the beam of a direct contact antenna 12 broadens significantly at such depths, thus making it difficult to obtain signal resolution which would be acceptable for measuring many restricted regions of the body.

This resolution problem is not significant when the device is applied for measuring lung water content, since the lung occupies a relatively large area and thus the broader beam is still directed at the proper body section. However, if it is desirable to measure a specific portion of the lung, or another part of the body, then an antenna which would permit a focusing of the beam would be desirable.

A typical focused antenna which could be utilized in this regard would utilize a focused aperture system including lenses or reflectors for focusing the emitted radiation into the antenna. Although such devices most commonly involve the use of noncontact antennas, the use of such a focusing system in contact with the body so as to permit impedance matching and temperature matching would be very desirable under many circumstances.

FIG. 6 illustrates the electronic circuitry 16 (see FIG. 1) of the radiometer of the preferred embodiment of the present invention. In this circuit, antenna 12 is connected through coaxial cable 14 to a coaxial switch 60 which is connected so as to be manually switchable between a temperature controlled reference load 62 and the antenna 12. Reference load 62 is comprised of a 50 ohm coaxial termination, and coaxial switch 60 is connected on its output side to a directional coupler 64. Coupler 64 is connected to an attenuator 66 which is connected to a noise source 68 for calibration purposes.

Directional coupler 64 and reference load 62 are also connected to separate switch positions of a diode switch 70 which includes a driver 72. Diode switch 70 is also connected to isolator 74 which is in turn connected to a radio frequency ("RF") amplifier 76 having a gain of approximately 20 decibels ("dB").

Amplifier 76 is connected to a double balanced mixer 78 which is also connected to a local oscillator 80. Local oscillator 80 produces a reference frequency so that by processing electrical signals from oscillator 80 with those from amplifier 76, the output of mixer 78 represents the original signal from antenna 12 except that it is lowered into the intermediate frequency ("IF") range. The output from mixer 78 is connected to IF amplifier 82 which has a typical gain of about 75 dB and a lower noise figure of approximately 2 to 3 dB.

Amplifier 82 is connected to diode detector 84 which is a crystal detector which is also connected to a synchronous detector 88. Synchronous detector 88 comprises a lock-in amplifier which is used to measure extremely small signals buried in noise. Such a lock-in amplifier is basically a phase sensitive detector which can be considered simply as a double pole, double throw reversing switch. By comparing an input signal with a reference signal, and ignoring all components of the signal which are not synchronized with it, nanovolt range signals can be measured in the presence of noise that is as much as 150 dB greater in amplitude.

In addition to removing the noise from a received signal, the reversing switch of detector 88, together with an output integrator (which is often included as part of the synchronous detector) transfers the received signal information from its input frequency to a corresponding direct current signal level. The time constant of the integrator can be made as long as necessary to provide the narrow bandwidth required to reject any noise which may be accompanying the signal.

Synchronous detector 88 is also connected to an oscillator 82 which transmits signals at a frequency of about 30 cycles per second. Oscillator 92 is also connected to driver 72 so as to contact diode switch 70. The oscillator 92 provides a timing means common to both diode switch 70 and synchronous detector 88 so that these devices may be caused to perform their proper functions in a synchronized manner with respect to each other. The output portion of synchronous detector 88 is connected to a suitable display/recorder device 90. Such display/recorder device 90 may, for example, comprise a strip chart recorder, such that the received signal is finally recorded on hard copy. Alternatively, the output of synchronous detector 88 can be connected to any one or more of the numerous other output devices which are available and used in the industry, such as cathode ray tubes, seven segment displays, liquid crystal diodes, or other similar electronic data read-out systems.

Specific examples of devices which are acceptable for use as the above-described circuit components and which are commerically available are presented in the following table:

| CIRCUIT COMPONENT | DRAWING REFERENCE NUMERAL | MANUFACTURER | PART NUMBER |
| --- | --- | --- | --- |
| Coaxial Switch | 60 | Teledyne Microwave | CS-31N6E |
| Load | 62 | NARDA | 43 70 DF |
| Directional Coupler | 64 | Hewlett Packard | 778D |
| Noise Source | 68 | International Microwave Corporation | NCR-1000-15 |
| Diode Switch | 70 | Alpha Industries | MT 3860 A |
| Insulator | 74 | Trak | 20A1371 |
| RF Amplifier | 76 | Avantek | ABG-2014M |
| Mixer | 78 | Technical Data | WJ-M1J |
| IF Amplifier | 82 | Trak Microwave SRC | 8400-1000 |
| Detector | 84 | Hewlett Packard | 8472A |
| Synchronous Detector | 88 | Princton Applied Research Corporation | 186 |

3. The Method of The Present Invention

Initially it should be noted that antenna 12 is constructed so as to approximate the impedance values of the animal bodies with which it will be used. The impedance of antenna 12 is affected by the internal area of housing 21, as well as by the physical size of ridge members 26 and 28. At a frequency of 1 GHz (which is used solely as an example), it has been found that an acceptable impedance value is 50 ohms. Thus, the antenna dimensions and ridge size are constructed so that the impedance of antenna 12 is in this range.

Upon placing antenna 12 in contact with an animal body, the impedance may be further modified by adjusting the position of rear plate 27 within housing 21. Further matching of the antenna impedance to that of the body may be accomplished by use of an interface material such as cellophane which is positioned between the antenna 12 and the body surface. The cellophane aids in the matching of the antenna impedance to that of the body by serving as a buffer between the two surfaces so as to reduce the effect of the impedance discontinuity between the body and antenna.

The radiometer circuit described in FIG. 6 constitutes one preferred embodiment of circuitry which may be utilized in practicing this invention. Of course, it will be recognized by one skilled in the art that there are numerous other radiometer circuits which may be available and which could be used in practicing this invention. Thus, the circuit of FIG. 6 is given only by ways of example since it is to be understood that such other circuits are considered to be within the scope of the invention as disclosed and claimed herein.

The radiometer circuit described in FIG. 6 can be calibrated by the following procedure: Noise source 68 transmits a signal through attenuator 66 and into directional coupler 64. Based on the known signal strength from noise source 68, an initial reference level corresponding to this unattenuated signal may be identified on display/recorder device 90. By adjusting attenuator 66 so as to cause attenuation of the signal from noise source 68, the display/recorder device 90 may be calibrated to identify the measured signal strength at various levels of attenuation. After calibration of the display/recorder device 90, the attenuation of radiometric signals measured by antenna 12 can be determined. Since the level of attenuation of the measured radiometric signals directly correlates to the emissivity of the lung, one may easily determine the change in amount of water contained within the lung by identifying changes in the emissivity of the lung.

After calibrating the circuitry, the remainder of the circuit elements may be tested by switching coaxial switch 60 so that it is connected through reference load 62. In this operating mode diode switch 70 sees the reference load on both inputs. If the circuit is responding properly, a straight line will be produced on display/recorder device 90.

With the circuitry calibrated and tested, and with antenna 12 positioned properly against the surface of a body, coaxial switch 60 is set so that the signals received by antenna 12 are transmitted through coaxial cable 14 to an input port of coaxial switch 60. The antenna signal travels through directional coupler 64 to one input of diode switch 70. Diode switch 70 switches between the signal from antenna 12 and reference load 62 in response to timed signals from driver 72 which occur at a predetermined rate (for example, 30 cycles per second) in accordance with the timing of signals from oscillator 92. By rapidly switching diode switch 70 between the signal from antenna 12 and reference load 62, the signal from antenna 12 can be calibrated with respect to the reference load 62 at a sufficient frequency to minimize errors due to changes in the gain of the various circuit components.

The signal from diode switch 70 passes into isolator 74 which only permits the through transmission of signals having a positive polarity. Thus, isolator 74 removes discontinuities in the signal from diode switch 70.

The signal from isolator 74 is amplified in RF amplifier 76 by a predetermined amount between about 20 and about 30 dB. By amplifying this signal, the effects of noise therein are reduced. From amplifier 76 the signal is transmitted into mixer 78, which is comprised of a diode arrangement and which also receives a signal from local oscillator 80. Mixer 78 reduces the frequency of the signal from amplifier 76 by an amount equal to the frequency of oscillator 80. Thus, by changing the oscillation frequency of oscillator 80 it is possible to detect different signal frequencies through antenna 12, thereby permitting more accurate characterization of body fluid content as a result of such multiple frequency measurements.

In this examplary system, local oscillator 80 is set to oscillate at a 1 GHz frequency, and thus the frequency of the signal from amplifier 76 is reduced by an amount of 1 GHz. As a practical matter, if the signal from amplifier 76 were at a frequency of 1.26 GHz, the signal transmitted from mixer 78 would then be at a frequency of 0.26 GHz. By reducing the signal frequency in this manner, a more manageable signal in the intermediate frequency range is created, although the lower frequency signal is still directly correlated to the original radiometric signal received by antenna 12.

The signal from mixer 78 is next amplified in IF amplifier 82, in order to further reduce problems caused by noise. Detector 84 places the signal from amplifier 82 into audio range. From detector 84, the signal is transferred to synchronous detector 88 which functions in response to oscillator 92 at a predetermined rate of up to 100,000 cycles per second. For purpose of illustration, the oscillator 92 will be discussed herein as oscillating at a frequency of approximately 30 cycles per second. It will be noted that since diode switch 70 allows the signal from antenna 12 to pass through only in alternation with the reference load 62, the signal from antenna 12 is only present for one half of each cycle. Thus, detector 88 indentifies that portion of the signal from detector 84 which correlates to the signal received from antenna 12.

Synchronous detector 88 also removes the noise from the signal and converts the signal from its input frequency into a corresponding direct current signal level. The signal which is transmitted from the synchronous detector 88 is received by display/recorder device 90, which produces a physical representation of this signal by recording a value corresponding to its intensity on paper or other suitable medium. Having a recorded value from display/recorder device 90, the system user may determine the emissivity of the body in the region being measured. By comparing this value with earlier recorded measurements, the user may identify any changes in the water content of the region being measured, as well as the actual volume of water which comprises this change. The physical relationships which permit identification of these conditions are described below.

If the emitting body is assumed to fill a flat halfspace, the emissivity "e" at normal incidence is given by:

$$e = 1 - \left| \frac{1 - \sqrt{\epsilon}}{1 + \sqrt{\epsilon}} \right|^2 \quad (1)$$

where the second term in equation (1) is the Fresnel reflection coefficient and $\epsilon$ is the dielectric constant of the emitter. By differentiating (1), the following equation for the change in emissivity as a function of the change in dielectric constant is obtained:

$$\delta e = 2(1 - e) Re\left(\frac{\delta \epsilon}{\epsilon^{3/2}}\right) \quad (2)$$

$\epsilon$ in the above equation is actually comprised of a combination of the various dielectric constants in the measured region. Thus, when measuring the lung, $\epsilon$ can be expressed as:

$$\epsilon_{lung} = F_b \epsilon_{blood} + F_t \epsilon_{tissue} + F_a \epsilon_o \quad (3)$$

where $F_b$ = percent blood volume
$F_t$ = percent tissue volume
$F_a$ = percent air volume
$\epsilon_o$ = dielectric constant of air.

By use of equation (2) it is possible to identify the change in total dielectric with respect to the measured change in emissivity of the lung. Further, in light of the relationship described by equation (3), if volume percentages of blood, tissue and air are known or can be approximated, then very accurate determinations of the amount and the change in lung water content can be made. Tables setting forth typical volume percentages required by equation (3) are readily available to those skilled in the art. For example, one table of such value is presented in Iskander and Durney, "Medical Diagnosis And Imaging Using Electromagnetic Techniques, Proceedings of NATO Advanced Study Institute On Theoretical Methods For Determining The Interaction of Electromaquetic Waves With Structures) at page 10, (Noawich, England, July 23, 1979).

The permittivity term $\epsilon$ is a complex number having both a real and an imaginary part. Thus, equation (2) is a single equation having two unknowns (the real part and the imaginary part of $\epsilon$). Although a knowledge of the magnitude of $\epsilon$ is adequate for most purposes, it is not possible to solve this single equation to determine the separate values of the complex terms in $\epsilon$. However, by making radiometric measurements at more than one frequency, multiple equations are developed since a different equation is necessary to describe each distinct frequency measured. Thus, by taking measurements at more than one frequency, it is possible to solve equation (2) for both components of $\epsilon$, thereby further increasing the accuracy of the fluid measurement.

It has been found that additional frequency measurements can be made in the millimeter wavelength range. This can be accomplished by use of an additional measuring device which is identical to the one described herein except that a millimeter wave antenna 13 (see FIG. 6) is substituted for microwave antenna 12 and one of the many types of wave-guides 15 well known in the art is substituted for coaxial cable 14. It will be readily appreciated that the electronic circuitry of the radiometer may be set up so as to allow for the convenient switching from the microwave antenna to the antenna responsive to millimeter frequencies. Measurements in the millimeter wave range identify the effects of radiation emitted by those portions of the body near the surface of the patient; therefore, by making such measurements, one is able to more accurately characterize the lung water content by identifying and eliminating the effects of the near surface radiation on the deeper microwave frequency measurements.

Unlike the invasive transmission of electromagnetic energy utilized by prior art measuring techniques, this invention is completely passive in application and noninvasive to the patient's body, yet produces measurements of much greater sensitivity and usefulness in the early diagnosis of medical abnormalities. Further, the prior art electromagnetic measurement techniques require both a transmitter and an antenna in order to function. As discussed above, that combination must be properly aligned and stabilized in order to obtain meaningful measurements, and this requires essentially complete immobilization of the patient in order to maintain the necessary alignment. The single antenna of this invention requires no alignment and provides accurate measurements without immobilization of the patient.

Accordingly, what is disclosed and claimed herein is a unique apparatus and method which permits the continuous monitoring of changes in water content within selected regions of animal bodies, without discomfort or danger to the body and with measurement capabilities sensitive enough that abnormalities or other important changes in body function may be diagnosed at very early stages.

It will be appreciated that the invention may be embodied in other specific forms without departing from its spirit or essential characteristics. The described embodiment is to be considered in all respects only as illustrative and not restrictive. The scope of the invention is, therefore, indicated by the appended claims rather than by the foregoing description. All changes which come within the meaning and range equivalency of the claims are to be embraced within their scope.

What is claimed and desired to be secured by United States Letters Patent is:

1. A method for measuring change in fluid content within an animal body comprising the steps of:
   obtaining an antenna means responsive to microwave radiation;
   positioning the antenna means so as to detect microwave radiation emitted from the animal body, wherein said microwave radiation corresponds to emissivity of the body in regions being monitored, with said emissivity being influenced by the fluid content within said animal body;
   emitting a signal from the antenna means which correlates to the microwave radiation detected by said antenna means and which corresponds to said emissivity;
   comparing the signals from the antenna means over time so as to identify changes in amounts of the microwave radiation detected by the antenna means and thus changes in the emissivity; and
   identifying change in the fluid content within the monitored region based on the changes identified in the emissivity of the monitored region.

2. A method as defined in claim 1 wherein the antenna means is responsive to radiation emitted from the animal body which has a frequency of from about 500 megahertz to about 12 gigahertz.

3. A method as defined in claim 1 further comprising the step of approximating impedance of the antenna means to impedance of the animal body.

4. A method for measuring changes in fluid content within selected regions of an animal body comprising the steps of:
   obtaining an antenna responsive to microwave radiation;
   positioning the antenna adjacent the animal body so as to detect microwave radiation emitted from the animal body, wherein said microwave radiation corresponds to emissivity of the body in regions being monitored, with said emissivity being influenced by the fluid content within said animal body;
   emitting a signal from the antenna which correlates to the microwave radiation detected by said antenna and which corresponds to said emissivity;
   comparing the signal from the antenna means over time so as to identify changes in amounts of the microwave radiation detected by the antenna means and thus changes in the emissivity; and
   identifying change in the fluid content within the monitored region based on the changes identified in the emissivity of the monitored region.

5. A method as defined in claim 4 further comprising the step of modifying impedance of said antenna so as to be substantially the same as that of said animal body.

6. A method as defined in claim 5 wherein the impedance of the antenna is modified by changing said antenna's interior physical dimension.

7. A method as defined in claim 4 wherein the antenna is responsive to radiation emitted from the animal body which has a frequency of from about 500 megahertz to about 12 gigahertz.

8. A method as defined in claim 4 wherein the antenna is responsive to radiation emitted from the animal body which has a frequency of from about 750 megahertz to about 1.5 gigahertz.

9. A method as defined in claim 4 wherein the antenna contacts the body and further comprising the step of maintaining the antenna at a temperature level which is approximately the same as that of said body.

10. A method as defined in claim 9 wherein the step of maintaining the antenna temperature comprises:
    (a) monitoring the body temperature;
    (b) monitoring the antenna temperature;
    (c) determining any temperature difference between the antenna and the body by reference to the temperatures monitored in steps (a) and (b); and
    (d) actuating heating means on the antenna when the temperature difference determined in step (c) indicates that the body temperature is higher than the antenna temperature.

11. A method as defined in claim 4 wherein the step of emitting a signal includes the step of presenting information which correlates to the signal emitted from the antenna on a cathode ray tube.

12. A method as defined in claim 4 wherein the step of emitting a signal includes the step of presenting information which correlates to the signal emitted from the antenna in printed form on hard copy material.

13. A method as defined in claim 4 wherein the step of emitting a signal includes the step of presenting information which correlates to the signal emitted from the antenna on an electronic data read-out system.

14. A method as defined in claim 4 wherein the step of emitting a signal includes the steps of:
    producing a signal corresponding to the radiation detected by the antenna means at a first measured frequency; and
    producing a signal corresponding to the radiation detected by the antenna means at one or more subsequently measured frequencies.

15. A method as defined in claim 14 wherein the step of producing a signal corresponding to the radiation detected at one or more subsequently measured frequencies includes the steps of:
    obtaining an antenna responsive to millimeter wave radiation;
    positioning the antenna adjacent the animal body so as to detect millimeter wave radiation emitted from the animal body, wherein said millimeter wave radiation corresponds to emissivity of the body in regions being monitored, with said emissivity being influenced by the fluid content within said animal body; and
    emitting a signal from the antenna which correlates to the millimeter wave radiation detected by said antenna and which corresponds to the emissivity.

16. A method for measuring changes in fluid content within selected regions of an animal body comprising the steps of:
    (a) obtaining an antenna responsive to microwave radiation and having and impedance which is similar to an impedance of the animal body to be measured;
    (b) connecting the antenna to electronic control circuitry;
    (c) connecting the antenna to a temperature control system for regulating temperature of said antenna;

(d) positioning the antenna upon a surface over the selected region of the body to be measured;
(e) monitoring the temperature of the body;
(f) monitoring the temperature of the antenna;
(g) actuating the temperature control means when the monitored body temperature is higher than the monitored antenna temperature so as to maintain the antenna at a temperature level which is approximately the same as that of said body;
(h) monitoring with the antenna the microwave radiation emitted from the body, wherein said microwave radiation corresponds to emissivity of the body in regions being monitored, with said emissivity being influenced by the fluid content within said body;
(i) emitting a signal from the antenna which correlates to the monitored radiation and which corresponds to the emissivity;
(j) processing the signal from the antenna in the electronic control circuitry; and
(k) comparing processed signals over time so as to identify changes in the amounts of radiation monitored by the antenna and thus changes in the emissivity; and
(l) determining the changes in the fluid content within the animal body based on the changes in the emissivity of the monitored region identified in the comparing steps.

17. A method as defined in claim 16 further comprising the step of adjusting the physical structure of the antenna so that the impedance of said antenna more closely approximates the impedance of said body.

18. A method as defined in claim 16 wherein said processing step (j) comprises the steps of:
receiving the signal from the antenna;
reducing the frequency level of the signal;
removing noise from the signal;
determining the magnitude of the signal; and
producing a signal corresponding to the magnitude of the signal from the antenna.

19. A method as defined in claim 16 wherein said monitoring step (h) includes the steps of:
monitoring with the antenna the microwave radiation emitted from the body at a first measured frequency; and
monitoring with the antenna the microwave radiation emitted from the body at one or more subsequently measured frequencies.

20. A method as defined in claim 19 wherein the step of monitoring the microwave radiation at one or more subsequently measured frequencies includes the steps of:
obtaining an antenna responsive to millimeter wave radiation; and
positioning the antenna adjacent the animal body so as to detect millimeter wave radiation emitted from the animal body, wherein said millimeter wave radiation corresponds to emissivity of the body in regions being monitored, with said emissivity being influenced by the fluid content within said animal body.

* * * * *

UNITED STATES PATENT AND TRADEMARK OFFICE
CERTIFICATE OF CORRECTION

PATENT NO.   : 4,488,559
DATED        : December 18, 1984
INVENTOR(S)  : Magdy F. Iskander It is certified that error appears in the above-identified patent and that said Letters Patent is hereby corrected as shown below:

Column 1, line 17, "sre" should be --are--

Column 1, line 47, "as" should be --has--

Column 4, line 17, "FIGS. 5" should be --FIG. 5--

Column 8, line 45, "82" should be --92--

Column 9, line 44, "ways" should be --way--

Column 10, line 58, "examplary" should be --exemplary--

Column 12, line 9, "Electromaquetic" should be --Electromagnetic--

Column 14, line 62, "and impedance" should be --an impedance--

Signed and Sealed this

Sixteenth Day of April 1985

[SEAL]

Attest:

DONALD J. QUIGG

Attesting Officer   Acting Commissioner of Patents and Trademarks